United States Patent
van Kempen

(10) Patent No.: US 7,893,070 B2
(45) Date of Patent: Feb. 22, 2011

(54) METHOD OF TREATING PARTURIENT PLACENTAL MAMMALS IN ORDER TO REDUCE MATERNAL AND/OR UTERINE EXHAUSTION

(75) Inventor: Theo van Kempen, Sint Stevens Woluwe (BE)

(73) Assignee: Provimi Holding B.V., Rotterdam (NL)

( * ) Notice: Subject to any disclaimer, the term of this patent is extended or adjusted under 35 U.S.C. 154(b) by 199 days.

(21) Appl. No.: 12/063,830

(22) PCT Filed: Aug. 14, 2006

(86) PCT No.: PCT/NL2006/050201

§ 371 (c)(1),
(2), (4) Date: Aug. 4, 2008

(87) PCT Pub. No.: WO2007/021189

PCT Pub. Date: Feb. 22, 2007

(65) Prior Publication Data

US 2009/0220617 A1    Sep. 3, 2009

Related U.S. Application Data

(60) Provisional application No. 60/707,954, filed on Aug. 15, 2005.

(30) Foreign Application Priority Data

Aug. 15, 2005 (EP) .................................. 05107485

(51) Int. Cl.
*A61K 31/522* (2006.01)
*A61K 31/137* (2006.01)
*A01N 43/74* (2006.01)
*A01N 33/02* (2006.01)

(52) U.S. Cl. .................. 514/263.34; 514/649

(58) Field of Classification Search ............... None
See application file for complete search history.

(56) References Cited

U.S. PATENT DOCUMENTS 4,748,022 A * 5/1988 Busciglio ............... 424/539
5,382,436 A * 1/1995 Potts ....................... 424/489
2003/0054015 A1   3/2003 Haze et al.
2004/0180077 A1   9/2004 Riker et al.
2004/0258765 A1  12/2004 Gee

FOREIGN PATENT DOCUMENTS

EP       0 958 821 A1      11/1999
WO       WO 93/04683   *    3/1993
WO       WO 2004/073420 A1  9/2004

OTHER PUBLICATIONS

Ness et al. (Medical Hypotheses 2001, 57, 310-312).*
Savineau (Europena Journal of Pharmacology 1988, 149, 187-190).*
Savineau et al. (Br. J. Pharmacol. 1990, 99, 261-266).*
Mitznegg et al. (Life Sciences 1970, 9, 975-981).*
Taggart et al. (Journal of Physiology 1998, 511, 133-144).*
Barger et al. (J. Physiol 1910, 41, 19-59).*
Phupong et al. Arch Gynecol Obstet 2007, 276, 167-170.*
Krandall, Bull. N.Y. Acad. Med. 1991, 67, 240-255.*
Infante-Rivard et al. JAMA 1993, 270, 2940-2943.*
G. Talosi, et al., "Inhibitory effects of methylxanthines on the pre-eclampic-like symptoms in ewes" *European Journal of Obstetrics & Gynecology and Reproductive Biology*, vol. 99, 2001, pp. 25-32.
V. Miljkovic et al., "Neurotherapy of infertility in cows caused by sickness of the uteine adnexa", *Acta Veterinaria*, vol. 43, No. 2-3, 1993, pp. 113-119.

* cited by examiner

*Primary Examiner*—Johann R Richter
*Assistant Examiner*—Jessica Kassa
(74) *Attorney, Agent, or Firm*—Gilberto M. Villacorta; Sunit Talapatra; Foley & Lardner LLP

(57) ABSTRACT

The present invention relates to a method of facilitating the birth process of placental mammals, especially to a method of reducing delays in the birth process and, thereby, complications resulting there from that may negatively affect the health and wellbeing of the mother and increase the incidence of stillbirths and/or neonatal mortality. According to the present invention delays in parturition that result from maternal and/or uterine exhaustion may be prevented or reduced by the administration of an effective amount of one or more psychomotor stimulants to the parturient mammal prior to and/or during parturition. Said psychomotor stimulant is selected from the group comprising xanthines and amphetamines.

11 Claims, 1 Drawing Sheet

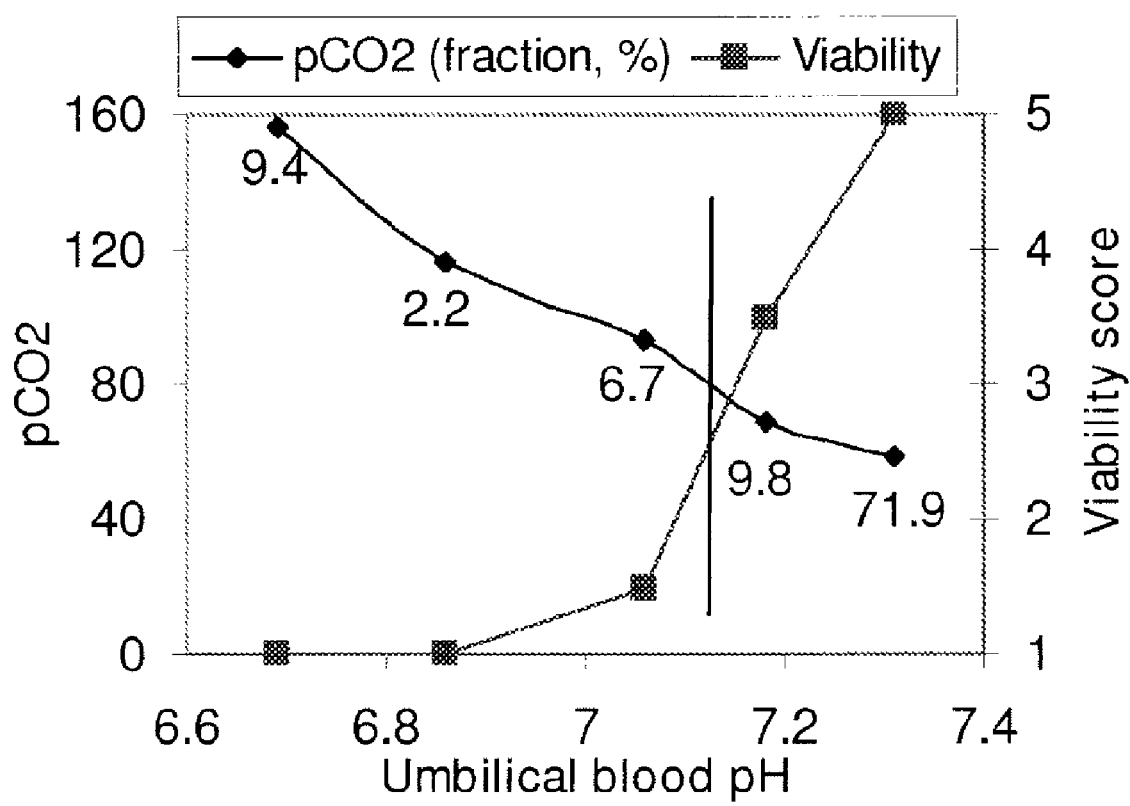

METHOD OF TREATING PARTURIENT PLACENTAL MAMMALS IN ORDER TO REDUCE MATERNAL AND/OR UTERINE EXHAUSTION

This is a U.S. National Stage application of PCT/NL2006/050201 filed Aug. 14, 2006, which claims priority to European application 05107485.4 filed Aug. 15, 2005 and U.S. Provisional application 60/707,954 filed Aug. 15, 2005.

FIELD OF THE INVENTION

The present invention relates to the field of parturition. More particularly, the present invention relates to a method of facilitating the birth process of placental mammals to reduce exhaustion-related complications during the birth process that may negatively affect the health and wellbeing of the mother and increase the incidence of stillbirths and/or neonatal mortality.

BACKGROUND OF THE INVENTION

A normal parturition process is divided into three stages. Among these stages, the first and second stages are directly involved in the delivery of fetus(es). The first stage of parturition begins with the onset of rhythmic uterine contraction and ends at the complete dilation of the cervix. The complete dilation of the cervix marks the beginning of the second stage of labor which ends immediately after the birth of the neonate(s). The third stage of labor extends from the birth of the neonate(s) to the complete expulsion of the placenta.

This labor progress is driven by two types of labor forces. The primary force is produced by the involuntary contractions of uterine muscle. The secondary force is produced by the increase of intra-abdominal pressure through voluntary contractions of the abdominal muscles and diaphragm. These forces cause an increase of intrauterine pressure to provide a critical expulsion force on the fetus. In humans, said primary uterine force should generate pressures of 50-60 mm Hg, with contractions of 50-60 sec duration and occurring at a frequency of every 2-3 min. The diaphragm and abdominal muscles in the second stage should be able to double the intra-uterine pressure in response to bearing-down sensations.

Exhaustion during labor can lead to the weakening of said primary and/or secondary force, increasing labor duration and eventually resulting in dystocia (arrest of labor). Two forms of exhaustion have been identified: uterine and maternal exhaustion. Uterine exhaustion is also referred to as 'secondary uterine inertia', which means that the uterine muscles are fatigued and are not producing meaningful contractions. Secondary Uterine Inertia (SUI) often occurs with persistent contractions, such as during fetal dystocia. It is also very likely to occur during the delivery of the last fetuses in a large litter. Maternal exhaustion refers to the inability to sufficiently increase intrauterine pressure by contractions of the abdominal muscles and diaphragm. This inability may not only be affected by the mothers' physiological state but also by her perception of effort and exhaustion.

Serious health complications may arise in the mother from exhaustion during labor. These include retained placenta, hypocalcaemia, hypomagnesaemia, metritis, and ketosis. This can result in health complications that require medical attention during parturition (e.g., forceps or vacuum extraction or caesarian sections) or after parturition (e.g., in case of hypocalcemia).

In the fetus, serious reductions of respiration may occur as a consequence of exhaustion and numerous clinical studies have correlated a prolonged labor duration and dystocia with many undesirable outcomes, including a higher rate of infant mortality, neonatal seizures, and postpartum hemorrhage, mainly as a result of oxygen deprivation of the fetus.

For example, for some fetuses the umbilical cord is broken before time of birth, e.g. in swine this concerns approximately 20% of the fetuses. If the cord was severed just before birth, it is usually of little consequence and the neonate is born healthy. If the parturient mother is having some difficulty delivering or is tiring out, fetuses are expelled at a slower rate. For fetuses with broken cords, this delay in birthing is often fatal as interruptions in blood flow and oxygen deprivation during periods of up to five minutes appear to be tolerated by fetuses, but beyond this, it results in metabolic damage that negatively affects health and can eventually cause stillbirth (Randall, 1971).

Another factor contributing to reductions of respiration of the fetus relates to uterine contractions intensifying as offspring are being delivered. Each contraction exerts pressure on the umbilical cord and may reduce blood flow to the fetus, thus reducing the amount of oxygen reaching the unborn. Especially if the birth process tends to become delayed or interrupted due to maternal exhaustion, the unborn fetus may die from suffocation as a result of these contractions and is presented as stillbirth.

Fetuses that are born alive but which have suffered a prolonged reduction in umbilical blood flow have disturbed metabolism and respiration, including elevated levels of $CO_2$ resulting in a decrease in blood pH. Randall (1971) showed that piglets born with an umbilical blood pH of 7.1 or lower had a low viability score. In Randall's study, 18.3% of piglets born had such low blood pH suggesting that dystocia is responsible for a large portion of neonatal mortality [Randall, G. C., The relationship of arterial blood pH and pCO2 to the viability of the newborn piglet. Can J Comp Med. 1971 April; 35(2):141-6].

For humans and large farm mammals like horses and cattle, exhaustion typically results in human intervention in the birth process. For example, oxytocin, oxytocin analogues, or oxytocin stimulants are injected to stimulate uterine contraction, or the fetus is extracted using e.g., forceps or vacuum extraction or using a caesarean section. In the UK in humans 18% of deliveries was by caesarean section, while 11.1% required instrumental deliveries (e.g., forceps and vacuum delivery). Although, most likely, these solutions are the only suitable alternatives given the conditions, mechanical interventions still can have serious implications for the health of the mother and the offspring and they may well be preventable with proper support of the mother. Furthermore, injections of oxytocin can actually be dangerous when the uterus is not properly dilated prior to administration of the intervention. Oxytocin can produce uterine spasm rather than rhythmical contractions resulting in fetal death in utero.

In the case of litter-bearing animals complications resulting from maternal and/or uterine exhaustion are even more likely to occur, whereas interventions may be less commonly available, and consequently the rate of stillbirth is much higher. For example, in swine an estimated 8% of fetuses are stillborn and 12% die shortly after birth. The incidence of low viable pigs (born weak) and stillborn pigs (intrapartum deaths) increases with birth order and with the length of parturition. It has been reported that the last pig born in a litter has a 50% chance of being stillborn, while an 11.8% perinatal mortality rate was observed in litters that farrowed in less than 6 hours, compared to 21.3% perinatal mortality rate in those litters that farrowed in more than 6 hours.

The beneficial effect of reducing farrowing intervals on stillbirth in sows was demonstrated by Rudloff and Bostedt, who studied the effect of the beta-adrenoceptor antagonist carazolol (Suacron) on farrowing in sows. In their study Rudloff and Bostedt showed that intravenous injection of 0.5 mg/50 kg bodyweight of carazolol reduced the rate of deliveries lasting more than six hours from 14.5 to 11.0%, resulting in reduced stillbirth rate from 8.3 to 7.1%, less necessity for external aid, decreased use of oxytocin, and diminishing occurrence of puerpal disorders. [Rudloff P R, Bostedt H., Effect of the beta blockader carazolol (Suacron) on parturition in sows. Tierarztl Prax. 1984; 12(4):443-449].

Preventing or reducing exhaustion may provide an interesting tool for reducing the incidence of postpartum and intrapartum morbidity or mortality, for reducing health complications in the mother resulting from exhaustive labor, and/or for reducing the need for external aid in parturient mammals. The present invention aims to provide a method of treating parturient mammals such as to realize these objectives.

SUMMARY OF THE INVENTION

The present inventors have now found that delays in parturition as a result of maternal and/or uterine exhaustion can be reduced by the administration of an effective amount of one or more psychomotor stimulants to the parturient mammal prior to and/or during parturition.

More in particular, the method of treatment provided by the present invention reduces the symptoms of exhaustion in mammals during parturition by administering one or more psychomotor stimulants selected from xanthines and/or amphetamines immediately preceding and/or during parturition, such that the need for possibly traumatic interventions in the birth process is reduced, the overall survival rate of neonates during and immediately after the birth process is increased and exhaustion-related health complications in the mother are reduced.

Amphetamines act by releasing mono-amines from nerve terminals in the brain. Nor-adrenaline and dopamine are the most important mediators in this connection, but 5-HT release also occurs with some amphetamines. The main pharmacological effects include locomotor stimulation and euphoria and excitement. In addition, amphetamines have peripheral sympathomimetic actions, producing a rise in blood pressure and inhibition of gastrointestinal motility.

Xanthines are CNS/psychomotor stimulants. At high concentrations, they can also decrease contractility of bronchial, vascular, and uterine smooth muscle, and stimulate respiration, diuresis, peripheral and coronary artery vasodilation, cerebral vasoconstriction, and cardiac muscle vasodilation. Some groups have reported so-called 'ergogenic effects' of xanthines, possibly involving modulating effects on carbohydrate metabolism and increases in contractility of skeletal muscle.

The xanthines thus constitute a class of substances with diverse pharmacological properties. The use of xanthines to reduce fatigue, i.e. improve mental performance and concentration, is well-known. Xanthines, especially theophylline, are also used as bronchodilators in severe asthmatic attacks while both caffeine and theophylline are used to prevent apnea in prematurely born infants. The physiological effects of xanthines have been subject of much investigation and several mechanisms of action have been demonstrated to be involved.

Xanthines are antagonists of adenosine, a compound that can inhibit both neuronal activity and behaviour through direct postsynaptic action on neurons and through indirect action involving presynaptic inhibition of neurotransmitter release. Xanthines can also inhibit phosphodiesterases, thus preventing inactivation of cyclic AMP and/or cyclic GMP. Elevated levels of cAMP and cGMP affect excitatory neurotransmitters such as norepinephrine and dopamine. Lastly, it has been reported that xanthines can modulate the conductance of several ion channels such as $Ca^{2+}$ and $Cl^-$ channels. The latter two effects of xanthines typically occur at higher concentrations than the first.

Although it is generally conceived that xanthines like caffeine may affect performance in prolonged exercise there is still much debate about the exact physiological events involved. Numerous studies have examined the effects of xanthines, especially caffeine, on peripheral and central events along the motor pathway, on metabolism, and on the cardiovascular system both during prolonged extensive exercise and during brief intense exercise. For example, it has been reported that caffeine ingestion increases the contractility of skeletal muscle [Tarnopolsky et al.: J. Appl. Physiol. 89: 1719-1724, 2000], alters muscle sensory processes, and reduces force sensation (leading to a 'willingness' to maintain near-maximal muscle activity longer [Plaskett et al.; J. Appl. Physiol. 91: 1535-1544, 2001]), increases plasma epinephrine concentrations (although the metabolic impact of this increase remains uncertain [Jackman et al.; J. Appl. Physiol. 81(4): 1658-1663, 1996]), and alters the cardiovascular response to dynamic exercise by augmenting regional blood flow [Daniels et al.; J. Appl. Physiol. 85: 154-159, 1998].

Xanthines have been demonstrated to inhibit oxytocin-stimulated uterine contractions in vitro, in (amongst others) isolated pregnant myometrium [Berg et al.; Am. J. Obstet. Gynecol. 156(4): 958-962, 1987], [Bird et al.; Am. J. Obstet. Gynecol. 157(1): 171-177, 1987], [D'Ocon M P; Arch Int Pharmacodyn Ther. 302: 268-279, 1989], [Savineau et al.; Br J. Pharmacol. 99(2): 261-266, 1990]. Moreover, theophylline and aminophylline have been tested and used clinically as a tocolytic agent because of their inhibitory action on uterine contractions [Lechner W.; Z Geburtshilfe Perinatol. 1986 November-December; 190(6):261-5], [Lipschiz J.; Am. J. Obstet. Gynecol. 131: 716-718, 1978]. Lipschitz studied the effects of administering aminophylline (250 mg, over five minutes) by intravenous infusion to women with oxytocin-induced contractions. He concluded that aminophylline exhibits poor uterine selectivity with an unfavorable cardiovascular/tocolytic ratio, such that this compound was unsuitable for delaying premature labor.

Despite the fact that xanthines have been considered to constitute suitable tocolytics it has now been found that they can advantageously be used for preventing and/or decreasing delays in parturition. Without wishing to be bound by theory, the present inventors hypothesize that these unexpected findings reside in the fact that for xanthines, the plasma concentration required for effective inhibition of uterine smooth muscle contractility is substantially higher than those required for psychomotor stimulation such that the unfavorable tocolytic effects of the xanthines are outweighed by the favorable effects on peripheral and central events along the motor pathway, on metabolism and/or on the cardiovascular system.

DESCRIPTION OF THE FIGURE

The enclosed FIGURE shows the relationship between umbilical blood pH, $pCO_2$, and viability in piglets.

DETAILED DESCRIPTION OF THE INVENTION

Thus, a first aspect of the present invention relates to a method of treating and/or preventing uterine and/or maternal exhaustion in a parturient placental mammal, said method comprising administering to said mammal an effective amount of one or more psychomotor stimulants selected from the group consisting of xanthines and amphetamines.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

The terms 'uterine exhaustion' and 'secondary uterine inertia', which are deemed to be synonyms and are used interchangeably herein, refer to the phenomenon that the uterine muscles are fatigued and are not producing meaningful contractions.

The term 'maternal exhaustion' as used herein refers to the phenomenon that the mother is unable to meaningfully increase intra-abdominal pressure through voluntary contractions of the abdominal muscles and diaphragm.

The term 'maternal dystocia' is also sometimes used to refer to uterine and/or maternal exhaustion. Maternal dystocia is usually defined as "difficult delivery or parturition caused by an abnormality or physical problem in the mother" and is not to be confused with 'fetal dystocia' (or 'shoulder dystocia') which is usually used to refer to a difficult delivery due to 'fetal malpresentation', which itself may cause uterine and/or maternal exhaustion.

As explained herein before, applying the present method will reduce the incidence of postpartum and intrapartum morbidity or mortality, reduce health complications in the mother resulting from exhaustive labor, and/or reduce the need for external aid in parturient mammals. Thus, the present invention also encompasses the use of the method as described herein for reducing the incidence of postpartum and intrapartum morbidity or mortality, reducing health complications in the mother resulting from exhaustive labor, and/or reducing the need for external aid in parturient mammals.

The present method may be advantageously used in any placental mammal in need of such treatment. Said mammal may for example be selected from humans, primates, equines, bovines, ovines, caprines, cervines, camelidea, canines, felines, and suidae. In a first preferred embodiment the mammal is a human. In another equally preferred embodiment the mammal is non-human, more preferably the mammal is a primate, equine, bovine, ovine, caprine, cervine, camelidea, canine, feline, or suidae, more preferably an equine, bovine, ovine or suidae. In still another preferred embodiment the mammal is a litter bearing mammal, preferably selected from suidae, ovine, feline, or canine.

The present method comprises the administration of an effective amount of one or more psychomotor stimulants selected from the group of xanthines, and amphetamines. The term 'xanthines' is commonly used in the art to refer to derivatives of xanthine. Thus the terms 'xanthines' and 'xanthine derivatives' are deemed to be synonyms and may therefore be used interchangeably herein. The most abundant and most used xanthine derivatives are methylxanthines. Thus, most preferably according to the invention said xanthines are methylxanthines. Suitable examples of methylxanthines include caffeine, theobromine, theophylline, aminophylline, enprofylline, dyfylline, pentoxifylline and paraxanthine.

The term 'amphetamines' as used herein refers to amphetamine and a group of compounds with pharmacological properties similar to amphetamine. The term 'amphetamines' thus includes amphetamine, dextroamphetamine, methylphenidate, fenfluramine and methylamphetamine.

The present invention also encompasses the use of pharmaceutically acceptable and/or edible salts, complexes and derivatives of the present psychomotor stimulants, precursors of the present psychomotor stimulants that are metabolized to the psychomotor stimulant after administration as well as bio-active metabolites of the present psychomotor stimulants.

Pharmaceutically acceptable and/or edible salts may include for example non-toxic acid addition salts formed from the psychomotor stimulant and an organic or inorganic acid recognized in the art as providing a pharmaceutically acceptable non-toxic acid addition salt of these compounds which are formed, e.g., theophylline hydrochloride and amphetamine hydrochloride. Since the aqueous solubility of xanthines tends to be low, reference to xanthines herein also includes water-soluble derivatives and complexes thereof. For example, the term theophylline includes the water-soluble compound aminophylline, which is formed by the combination of theophylline with ethylenediamine (2:1).

Suitable examples of substances that metabolize to methamphetamine or amphetamine in the body include amphetaminil, benzphetamine, clobenzorex, deprenyl, dimethylamphetamine, ethylamphetamine, famprofazone, fencamine, fenethylline, fenproporex, furfenorex, mefenorex, mesocarb, and prenylamine. Theophylline, theobromine, and paraxanthine which, as mentioned herein before, are themselves psychomotor stimulants are also metabolites of caffeine. Thus, where in the description a psychomotor stimulant is mentioned, its salts and/or precursors, and/or bio-active metabolites are also encompassed.

According to a preferred embodiment, the present psychomotor stimulant is a xanthine, preferably a methylxanthine. Contrary to amphetamines, xanthines do not induce euphoria, stereotyped behavior patterns or a psychotic state. Xanthines and amphetamines can pass the placental barrier. As mentioned before, several methylxanthines have been used clinically as tocolytics and adverse side-effects, especially with regard to the newborns have not been reported so far. Therefore, it is particularly preferred to use one or more methylxanthines according to the present method.

Moreover, caffeine, theophylline, and paraxanthine are routinely used in (prematurely) born infants as a safe and efficacious means to treat apnea (e.g., Gannon; Neonatal Netw. 19(8): 33-36, 2000). Transmission of methylxanthines from mother to offspring should thus not be considered a risk for the neonate and may actually further improve survival chances of the neonate. Therefore, in a particularly preferred embodiment of the present invention the method comprises administering caffeine, theophylline, paraxanthine or mixtures thereof to the parturient mammal.

As mentioned herein before, xanthines have a variety of pharmacological effects, some of which may advantageously contribute to reducing delays in the birth process and some of which can be described as tocolytic. It is hypothesized that different pathways, i.e. different molecular mechanisms, are involved in these different pharmacological effects, i.e. adenosine antagonistic actions and phosphodiesterase inhibiting effects. According to the present invention it is particularly preferred to use xanthines that are relatively potent adenosine receptor antagonists and/or relatively weak phosphodiesterase inhibitors. Therefore, according to a preferred embodiment the psychomotor stimulant is a xanthine selected from the group of caffeine, theophylline, paraxanthine and mixtures thereof. According to a most preferred embodiment the one or more psychomotor stimulants are selected from caffeine, theophylline and mixtures thereof.

The relative potencies of the naturally occurring methylxanthines such as caffeine, theophylline and paraxanthine as adenosine receptor antagonists and phosphodiesterase inhibitors can be modulated by replacing the substituents at 1-, 3- and 7-positions thereof. Some of these analogs may therefore be particularly suitable for use in the present method. Analogs of caffeine and theophylline that are known to be more potent adenosine receptor analogs and relatively weak phosphodiesterase inhibitors include for example 1,7-dimethyl-3-propargylxanthine, 3,7-dimethyl-1-propargylxanthine and 1,3,7-tripropargylxanthine [Choi et al.; Life Sci. 43: 387-98 (1988)]. The use of such analogs is also encompassed by the present invention. According to the invention, the method comprises administering the present psychomotor stimulant to said placental mammal in order to reduce uterine and/or maternal exhaustion during parturition. As explained herein before uterine and/or maternal exhaustion become particularly relevant towards the end of the first stage (dilation of the cervix) and during the second stage (expulsion of the fetus) of the birth process. Therefore it is particularly preferred that the peak plasma levels of the one or more xanthines and/or amphetamines are reached during or shortly after the period between transition from the first to the second stage and before transition from the second to the third stage. Therefore, according to a preferred embodiment the method comprises administering the one or more psychomotor stimulants during the interval starting 12 hours prior to the commencing of parturition and ending at the moment of birth the last fetus. More preferably the method comprises administering the one or more psychomotor stimulant during the interval between the dilation of the cervix and the moment of birth of the first neonate.

Without wishing to be bound by it, it is hypothesized that, due to the specific pharmacokinetic properties of xanthines, especially caffeine, found in pregnant sows, administering the effective amount of the one or more xanthines 4-10 hours or more preferably 6-8 hours before commencing of parturition would represent the optimal, most preferred method of treatment, as will be illustrated in the examples hereafter. However, as will be clear to the skilled person, this precise optimal regimen may be difficult to exactly comply with. Other, sub-optimal regimens may therefore be applied without departing from the scope of the invention.

According to the present invention, 'an effective amount' refers to an amount that is sufficient to elicit a beneficial therapeutic effect. In the present method said beneficial effect refers to any physiologic and/or psychological effect leading to reduction of delays or interruptions of the birth process. Such physiologic and/or psychological effects may for example involve the mother's ability to voluntarily contract the abdominal muscles and diaphragm, uterine contractility, and the mothers perception of effort. Especially in litter-bearing mammals the effect of exhaustion can be recognized by the increase of the intervals between subsequent births. It will be recognized by the skilled person that the effective amount of the one or more stimulants used in the present method may vary according to factors such as the physiological state, age, and weight of the subject, and the ability of the specific active compound to elicit a desired response in the subject. Thus dosage regimens can be determined and adjusted by trained medical or veterinary personnel to provide the optimum therapeutic effect. Furthermore, an effective dosage is one in which any toxic or detrimental effects of the active compound are outweighed by the therapeutically beneficial effects.

According to one embodiment of the invention wherein the present psychomotor stimulant is an amphetamine, the peak plasma concentration does not exceed 1 mM, preferably it does not exceed 100 µM. According to a particularly preferred embodiment the plasma concentration ranges from 0.01 µM-1 mM, preferably from 0.1-100 µM such that the dosage to be administered ranges from 0.001-10 mg/kg per 5 hours, preferably 0.01 to 1 mg/kg per 5 hours, more preferably from 0.05 to 0.5 mg/kg per 5 hours.

In a particularly preferred embodiment, the present psychomotor stimulant is a xanthine, more preferably a methylxanthine, and an effective amount is an amount which is sufficient for attaining a plasma concentration at which the tocolytic effects are outweighed by the advantageous effects resulting from cardiovascular stimulation, increased contractility of skeletal muscle and/or stimulation of central and peripheral psychomotor function. Still more preferably, the effective amount of the one or more methylxanthines does not exceed an amount necessary to attain the plasma threshold level for phosphodiesterase inhibition mediated physiological effects.

Accordingly, in a first preferred embodiment wherein the present method comprises administering caffeine, it is preferred that the plasma concentration of caffeine and its pharmacologically active metabolites does not exceed 500 µM, preferably it does not exceed 100 µM. It is even more preferred that said plasma concentration ranges from 1 to 50 µM Thus, said method preferably comprises administering caffeine in a dosage of 0.01-10 mg/kg bodyweight per 12 hours, more preferably 0.05-10 mg/kg bodyweight, most preferably 0.1-7 mg/kg bodyweight. Said dosage can be given both as a rapid/immediate release formulation and as a slow/controlled release formulation.

According to another equally preferred embodiment wherein the present method comprises administering paraxanthine, the plasma concentration of paraxanthine and its pharmacologically active metabolites does not exceed 500 µM. It is even more preferred that said plasma concentration ranges from 1 to 50 µM. Thus, said method preferably comprises administering paraxanthine in a dosage of 0.01-10 mg/kg bodyweight per 12 hours, more preferably 0.05-10 mg/kg bodyweight, most preferably 0.1-7 mg/kg bodyweight.

According to still another embodiment, wherein the present method comprises administering theophylline, the plasma concentration of theophylline and its pharmacologically active metabolites does not exceed 500 µM. It is even more preferred that said plasma concentration ranges from 1 to 50 µM. Thus, said method preferably comprises administering theophylline in a dosage of 0.01-10 mg/kg bodyweight per 12 hours, more preferably 0.05-10 mg/kg bodyweight, most preferably 0.1-7 mg/kg bodyweight.

According to a particularly preferred embodiment, the present method comprises the co-administration of one or more additional active ingredient selected from $Ca^{2+}$, $Mg^{2+}$, $K^+$, $Zn^{2+}$, $Na^+$, phosphate, sulphate, chloride, Vitamin K, Vitamin E, nicotinic acid, carnitine, taurine, and ascorbic acid. According to an even more preferred embodiment the present invention comprises the co-administration of two or more, more preferably of three or more and most preferably of four or more of said additional active ingredients. The $Ca^{2+}$, $Mg^{2+}$, $K^+$, $Zn^{2+}$, $Na^+$, phosphate, sulphate and/or chloride are preferably co-administered in the form of their salts, such as NaCl, KCl, $MgSO_4$, $CaHPO_4$ and $ZnSO_4$. It was found that the efficacy of the present psychomotor stimulant in reducing delays in the birth process as a result of uterine and/or maternal exhaustion could be further improved by the co-administration of these additional ingredients.

According to a particularly preferred embodiment the present invention comprises the co-administration of $K^+$, $Ca^{2+}$ and/or $Mg^{2+}$, most preferably the method comprises the co-administration of $K^+$, $Ca^{2+}$ and $Mg^{2+}$.

Preferably the aforementioned additional ingredients are administered together with the one or more psychomotor stimulants, still more preferably they are administered in a single preparation.

According to a particularly preferred embodiment the present method comprises the co-administration of NaCl in an amount of between 0.02-20 mg/kg, preferably 0.1-10 mg/kg bodyweight, KCl in an amount of between 0.02-20 mg/kg, preferably 0.1-10 mg/kg bodyweight, $MgSO_4$ in an amount of 0.1-50 mg/kg, preferably 0.5-30 mg/kg bodyweight, $CaHPO_4$ in an amount of between 0.2-250 mg/kg, preferably 1-100 mg/kg bodyweight, $ZnSO_4$ in an amount of 0.01-50 mg/kg, preferably 0.05-20 mg/kg bodyweight, ascorbic acid in an amount of between 0.002-25 mg/kg, preferably 0.01-5 mg/kg bodyweight, taurine in an amount of between 0.2-100 mg/kg, preferably 1-50 mg/kg bodyweight, carnitine in an amount of between 0.01-25 mg/kg, preferably 0.05-5 mg/kg bodyweight, nicotinic acid in an amount of between 0.002-25 mg/kg, preferably 0.01-5 mg/kg bodyweight, vitamin E in an amount of between 0.01-25 mg/kg, preferably 0.05-5 mg/kg and/or vitamin K in an amount of between 0.001-5 mg/kg, preferably 0.005-1 mg/kg bodyweight.

It was furthermore found by the inventors that the efficacy of the present method can be even further improved if creatine is administered to the mother in the days preceding parturition. Creatine is involved in high-energy phosphate metabolism, acting as an 'energy-buffer' inside the cell. Thus, energy generated in the form of ATP can be temporarily transferred to creatine forming phosphorylcreatinine. This energy reserve can be utilized in time of high energy demand or when the oxygen supply is reduced. Creatine thus enables intense physical activity to persist longer.

Therefore, according to a particularly preferred embodiment, the present method comprises the loading of the mother with creatine in the days preceding parturition. More particularly, the present method comprises the administration of an effective amount of creatine within the period of 100 days to 1 hour before parturition, more preferably within the period of 50 days to 12 hours before parturition, most preferably within the period of 20 to 1 days before parturition. Preferably the total amount of creatine administered during said interval ranges from 0.01-100 g/kg, more preferably 0.05-50 g/kg, most preferably 0.1-10 g/kg.

According to an even more preferred embodiment the method comprises administering creatine in a dosage regimen of 0.001 to 10 g/kg per 24 hours, more preferably 0.01 to 5 g/kg per 24 hours most preferably 0.05 to 1 g/kg per 24 hours during said interval.

According to the present invention it is preferred that the present one or more psychomotor stimulants and optionally the one or more additional ingredients, are administered via the oral, buccal, rectal, transdermal, subcutaneous, or intravenous route. Most preferably the one or more psychomotor stimulants are administered via the oral route. Thus, suitable compositions comprising the one or more psychomotor stimulants for use in the present method can be a solid, a liquid, a paste, or a gel. Solid form preparations include powders, tablets, dispersible granules, capsules, sachets, and suppositories. A solid carrier can be one or more substances which may also act as diluents, flavoring agents, solubilizers, lubricants, suspending agents, binders, energy sources, or tablet disintegrating agents; it can also be an encapsulating material. In powders, the carrier is a finely divided solid which is in admixture with the finely divided active component. In tablets and suppositories the active component is mixed with the carrier having the necessary binding properties in suitable proportions and compacted in the shape and size desired. The powders, tablets and suppositories preferably contain 0.01% to about 70% of the active component. Suitable carriers are carbohydrates like lactose, sugar, pectin, dextrin, starch, tragacanth, methyl cellulose, sodium carboxymethyl cellulose, or a low-melting wax and the like.

Liquid form preparations include solutions, suspensions, and emulsions. Sterile water or water-propylene glycol solutions of the active compounds may be mentioned as an example of liquid preparations suitable for parenteral administration. Liquid preparations can also be formulated in aqueous polyethylene glycol solution.

Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material.

Preferably the formulation has the form of a paste or a gel, i.e. a thickened or gelled aqueous composition, said thickened or gelled composition comprising as a carrier a mixture of water and a thickening and/or gelling agent. Suitable examples of thickening and/or gelling agents include fumed silica, glycerine, polysaccharide hydrocolloids such as carrageenan, alginates, pectines, agar, cellulose and cellulose derivatives, gums, starches, glucan, curdlan, and thickening and/or gelling proteins such as gelatin and caseinates. The ratio of water and thickening agents used will depend on the specific type of thickening agents used and on the exact viscosity or gel strength desired. Typically, the carrier will comprise at least 0.1 wt %, preferably at least 0.5 wt %, more preferably at least 1.0 wt %, most preferably at least 2.5 wt % of said thickening and/or gelling agent. The amount of water may range from 5-99.9 wt % based on the total weight of the carrier.

According to a particularly preferred embodiment the active ingredient(s) of the present invention is/are provided in a carrier comprising mono-, di- and/or trisaccharides. Mono-, di- and trisaccharides, besides providing a suitable carrier in admixture with water, may at the same time serve as an energy source that may further aid to the efficacy of the present method. Typically, in case the carrier comprises mono-, di and/or trisaccharides, they are incorporated in an amount of at least 1.0 wt %, preferably 2.5 wt %, more preferably 5 wt %, based on the total weight of the carrier.

The carrier may furthermore comprise additional ingredients such as preservatives, humectants, substances for improving taste or smell, texture-improving agents and/or substances that improve the appearance of the composition.

Preferably the present active components, i.e. the one or more psychomotor stimulants, optionally combined with the additional active ingredients, as well as the (optional) creatine, are provided in preparations in unit dose formulation. In such formulation, the active ingredient(s) are provided in physically discrete units suitable as unitary dosage, each unit containing a predetermined quantity of said active ingredients. Thus typically, a composition comprising the active ingredient(s) is divided into unit doses containing appropriate and fixed quantities of said ingredient(s) which are packaged as discrete units. Packaged preparations may contain one or more of these discrete quantities. Suitable examples include tablets or suppositories in a blister package or liquids, pastes, gels and powders in vials or ampoules or other types of containers. Based on the dosages described here above, the skilled person will be able to determine appropriate quantities, depending on the (average) body weight of the mammal for which the unit dosage form is provided.

According to a particularly preferred embodiment the present composition is a nutraceutical. The term "nutraceutical" is commonly used in the art and is usually defined as 'a product isolated or purified from foods, and generally sold in medicinal forms not usually associated with food and demonstrated to have a physiological benefit or provide protection against chronic disease'. Caffeine, theophylline, and theobromine are naturally occurring and can be found in several species of plants. The present nutraceuticals may for example comprise extracts of such plants.

According to a particularly preferred embodiment, the present composition comprises green tea extract (extract from *Camellia sinensis*), preferably containing at least 1% of caffeine.

A particularly preferred embodiment relates to a composition in the form of a paste or a gel, said composition comprising 0.01-70 wt %, more preferably 0.05-50 wt %, still more preferably 0.1-20 wt %, of the present one or more psychomotor stimulants and at least 30 wt %, preferably at least 50 wt %, more preferably at least 80 wt % and most preferably at least 95 wt %, of a carrier, as described herein before. According to a most preferred embodiment the present composition furthermore comprises one or more additional ingredients selected from $Ca^{2+}$, $Mg^{2+}$, $K^+$, $Zn^{2+}$, $Na^+$, phosphate, sulphate, chloride, vitamin K, vitamin E, nicotinic acid, carnitine, taurine and ascorbic acid, as defined herein before.

Preferably, the aforementioned composition is in unit dosage form, as explained herein before. Thus typically the present composition is a unit dose at least comprising 10 mg of the one or more psychomotor stimulants, preferably at least 20 mg, more preferably at least 50 mg.

An even more preferred embodiment of the present invention relates to a composition as described herein before for administration to placental mammals, preferably selected from primates, equines, bovines, ovines, caprines, cervines, camelidae, suidae, felines, and canines. Even more preferably the invention relates to a nutraceutical preparation in unit dose formulation for administration to large animals prone to dystocia such as equines, bovines, ovines, and suidae such that the a unit dose comprises the one or more psychomotor stimulants in an amount of at least 100-2000 mg, preferably 200-1500 mg, most preferably 500-1000 mg. Another aspect of the present invention relates to a kit comprising at least one preparation containing a unit dose of the present psychomotor stimulant as described herein before as well as at least one preparation containing a unit dose of creatine. Preferably said kit comprises at least two, more preferably at least three and most preferably at least four of said preparations containing a unit dose of creatine. Such a kit can conveniently be used in a method of facilitating parturition in humans or farm animals as described herein before.

Another aspect of the present invention relates to a kit comprising at least one preparation containing a unit dose of the present psychomotor stimulant as described herein before as well as a preparation comprising an active component that can be used to induce parturition. The active component that can be used to induce parturition is preferably selected from the group of oxytocines, prostaglandines, anti-progestogens, and relaxin. Such a kit can conveniently be used in a method of facilitating parturition in farm animals. It provides the particular advantage that parturition can be induced at the time that personnel are present such as to ascertain that the animals receive the present psychomotor stimulant at the right time.

The invention will be further illustrated by means of the following non-limiting examples.

EXAMPLES

Example 1

A nutraceutical composition according to the present invention was prepared in the form of a paste for oral administration, using green tea extract. The nutraceutical was provided in unit dosage form suitable for use in swine having an average body weight of around 250 to 400 kg. Thus each unit dose comprises 4.0 g of Green Tea extract, comprising 10 wt % of caffeine, which extract is uniformly mixed with 41 g of a carrier composition containing, based on the total weight of the carrier, 57 wt % of water, 28 wt % of glycerin, 5 wt % of glucose syrup, and 10 wt % of sorbitol. $MgSO_4$, $CaHPO_4$, KCl and NaCl were also incorporated into the composition in accordance with the invention. The obtained unit doses were packaged in separate containers and can suitably be used in accordance with the invention. The unit doses can be administered at once or in several portions during the parturition process.

Another neutraceutical composition in accordance with the invention was prepared in the same manner, except that 1.8 g of a 50% green tea caffeine extract was used instead of 4.0 g of the extract containing 10 wt % of caffeine, such that each unit dose comprised approximately 900 mg of caffeine instead of 400 mg.

Example 2

In commercial swine production, typically 8% of the fetuses are stillborn, and 12% of the newborn piglets die prior to weaning (SIVA, 2005). Oxygen deprivation during the birth process is an important causal factor for both stillbirths and neonatal mortality. An indicator for oxygen deprivation is umbilical (blood) pH. This pH is typically 7.4, but upon oxygen deprivation $CO_2$ accumulates in the blood and tissues resulting in a drop in pH. If this drop is severe enough, it will result in the death of the fetus. A moderate drop in pH may not be lethal but may inflict sufficient metabolic damage such that it affects the health and fitness of the newborn and thus its chances of survival. Measurements of umbilical (blood) pH confirmed that this pH drops as the length of parturition increases. Previous work by Randall (1971) has shown a good correlation between umbilical pH and livability of piglets (FIG. 1).

Infrared radiation temperature is another indicator of metabolic health of a mammal. A strong correlation between infrared temperature and survival chances for newborn pigs has been shown. This infrared temperature was obtained by collecting piglets at birth, immediately drying them, and measuring infrared temperature. In a first experiment, 7 sows received a caffeine-comprising suppository (1-2 mg/kg BW, or 400-600 mg) after the birth of the first piglet in a litter. The indices of piglet health as described here above were compared to those of a control group of 6 sows. It was found that due to caffeine administration to the sow piglet umbilical (blood) pH increased with 0.044±0.020 units, (P=0.03) and radiation temperature increased with 0.60±0.29° C. (P=0.04).

Birth interval between subsequent piglets increased significantly by 9 minutes for each hour into parturition (P<0.01)

in control sows, while it was not affected by the time from the start of parturition in sows that received caffeine (numerical increase of 3.6 minutes for each hour into parturition, P=0.11).

This trial thus shows that caffeine improved the indices of piglet health that were previously shown to be directly correlated with piglet survival.

Example 3

In a second experiment, 19 sows received 400 mg of caffeine comprised in a paste for oral ingestion, in accordance with the invention, after the birth of the first piglet while 19 sows served as untreated controls.

It was shown that the administration of caffeine resulted in a shortened time interval between the birth of the first and $10^{th}$ piglet in each litter, decreasing from a mean of 159 minutes for the controls to 110 minutes for the treated animals. The distributions in this time parameter were significantly different between these two groups of animals, with the controls showing a skewed distribution and strong kurtosis. Practically, some untreated animals delivered their litter expediently and with few problems, but there were a substantial number of mothers for whom parturition became a lengthy process. In the treated animals, a distribution much closer to normal and with a lower mean was observed suggesting that on average parturition proceeded much faster but there were also less sows with excessively long parturitions.

Example 4

Compositions in accordance with the invention, which comprised green tea extract or pure caffeine that was added as such, in sufficient amounts to provide either 470 or 940 mg of caffeine were administered to 16 pregnant sows (mid gestation). Blood samples were collected pre-administration and at multiple time points post administration through an ear-vein catheter such that the uptake of caffeine into the blood (serum) could be modelled. Besides the caffeine level, the levels of its main metabolites paraxanthine, theophylline, and theobromine were determined.

Prior to administration of the treatment compositions the animals had very low levels of the different methylxanthines in their blood. Average values were 0.04 mg/L for caffeine and theobromine, and 0.01 mg/L for theophylline. These data suggest that conventional swine feed contains minute amounts of methylxanthines.

Following administration of the treatment compositions, a two-compartment distribution of caffeine was observed: the first compartment showed a very rapid uptake and loss over time, which is hypothesized to represent the uptake of caffeine from the intestines into blood after which it more slowly equilibrates with the rest of the body. This pool was not modelled. The second compartment exhibited a much slower uptake and decay over time.

For the second compartment, peak blood concentrations were observed 8 hours post administration. These were nearly 5 μM for caffeine and 3 μM for green tea when 940 mg of caffeine was administered (and half that for the 470 mg dose), suggesting that the bio-availability differed between compositions based on green tea and on pure caffeine. Based on the assumption that caffeine distributed itself in 60% of the animals body mass, bio-availability was estimated at 44% for caffeine and 28% for green tea, the bioavailability for green tea was equal to approximately 60% of that of caffeine.

It was furthermore found that mean plasma half-life of the caffeine was longer than what had been expected beforehand. Mean plasma half-life of caffeine was statistically the same for all products at about 22 h, which is significantly longer than that reported in literature for non-pregnant sows. Differences in caffeine clearance under hormonal influence in other mammal species, e.g. during the menstrual cycle, during pregnancy or during hormonal treatment such as contraceptive treatment or hormone replacement therapies, had been reported previously. The observed increase in plasma half-life may therefore, without wishing to be bound by this theory, well be ascribable to hormonal effects.

Presuming that expulsion of the fetuses is the period during which exhaustion of the parturient sow poses the greatest risk, and that caffeine has its largest effect during this process, it was concluded that the optimum time of administration of the treatment composition is approximately 6 to 8 hours before the start of parturition.

Example 5

The method of treatment according to the present invention was further tested at the Provimi research station in Velddriel, the Netherlands, in three farrowing groups. In the Velddriel facility farrowings are not attended by (veterinary) personnel and parturition is thus not actively managed. Stillbirth and mortality rates are thus in line with commercial practices.

Sows were assigned to treatment based on parity. Overall, 27 sows served as controls and 29 were treated in accordance with the present invention when they were expected to farrow in the next 8 hours. Treated sows were administered 900 mg of caffeine comprised in a paste for oral ingestion, in accordance with the invention.

Control sows had 0.89 stillbirths per litter and 1.15 piglet per litter died (without identifiable cause) or was euthanized for being weak shortly after parturition. In contrast, in the treated group 0.31 piglets per litter were stillborn and 0.48 piglets per litter died or were euthanized for being weak after parturition.

In order to assess whether caffeine was transferred from the mother to the piglets, blood samples were collected from several piglets at the time of birth and samples from colostrum were taken. Analysis of these samples showed that caffeine transfers to the piglet in utero and also via the colostrum. The concentrations found were dependent on the time relative to dosing the treatment composition. For piglets at birth, they were roughly $\frac{1}{4}^{th}$ the concentration in the mother at that time-point, and in milk they were roughly $\frac{1}{6}^{th}$ the concentration in the mother at that time-point. Values observed were in the range of 0.1 to 1.5 mg/L.

Example 6

The method of treatment according to the present invention was further tested at a well-managed farm in Bieganow, Poland. In this facility farrowings are attended by (veterinary) personnel and parturition is actively managed. As a result, stillbirth rates are extremely low (0.33 piglets per litter or 3% of the piglets).

At this farm, 89 sows comprising one farrowing group were available for the test. These sows were assigned to receive either a 900 mg of caffeine containing paste in accordance with the invention or no treatment, based on parity, body condition, and historical performance. The treatment composition was administered orally to selected sows when they were expected to farrow in the next 8 hours.

Likely as a result of this active management, no statistically significant differences in stillbirths were seen between the two treatment groups. However, there was a higher assistance rate (26%) in the control group than in the treated group (18%). In the control group, seven sows required medical care post-farrowing (one of which died) while no sows required medical care in the control group. The treated group was observed to consume more feed post farrowing. This is likely the result from the farrowing process having been less taxing. This increase was 14% on the first day post farrowing and 10% for the first five days post farrowing. At weaning, piglets from treated sows were 9% heavier than controls, most likely as a result of this increase in feed intake compared to the control group.

The invention claimed is:

1. A method of treating or preventing uterine and/or maternal exhaustion in a parturient mammal comprising administering to the mammal an effective amount of a psychomotor stimulant selected from the group consisting of xanthines and amphetamines.

2. The method according to claim 1, wherein the psychomotor stimulant is caffeine, theobromine, theophylline, paraxanthine, aminophylline, enprofylline, amphetamine, methylphenidate, fenfluramine, methylamphetamine, or mixtures thereof.

3. The method according to claim 2, wherein the psychomotor stimulant is caffeine, paraxanthine, theophylline, or a mixture thereof.

4. The method according to claim 1, in which the psychomotor stimulant is administered to the mammal during the interval 12 hours prior to the commencing of parturition and the moment of birth of the last fetus.

5. The method according to claim 1 further comprising administering an effective amount of creatine within 100 days to 1 hour before parturition.

6. The method according to claim 1, in which the administration is oral, buccal, rectal, transdermal, subcutaneous, or intravenous.

7. The method according to claim 6, in which the administration is oral.

8. The method according to claim 1, in which the mammal is litter bearing, a primate, equine, bovine, caprine, cervine, or camelidea.

9. The method according to claim 8, in which the primate is a human.

10. The method according to claim 8, in which the litter bearing mammal is suidae, ovine, feline, or canine.

11. The method according to claim 1 further comprising administering to the mammal $Ca^{2+}$, $Mg^{2-}$, $K^+$, $Zn^{2+}$, $Na^+$, phosphate, sulphate, chloride, Vitamin K, Vitamin E, nicotinic acid, carnitine, taurine, ascorbic acid, or combinations thereof.

* * * * *